(12) United States Patent
Stuchlik et al.

(10) Patent No.: US 8,426,459 B2
(45) Date of Patent: Apr. 23, 2013

(54) COMPOSITION OF FLAVANOLIGNAN AND AMINO ACID WITH IMPROVED WATER SOLUBILITY

(75) Inventors: Milan Stuchlik, Opava (CZ); Jiri Kopenec, Strelske Hostice (CZ)

(73) Assignee: Agra Group, A.S., Strelske Hostice (CZ)

(*) Notice: Subject to any disclaimer, the term of this patent is extended or adjusted under 35 U.S.C. 154(b) by 164 days.

(21) Appl. No.: 13/000,607

(22) PCT Filed: Jun. 22, 2009

(86) PCT No.: PCT/CZ2009/000086
§ 371 (c)(1), (2), (4) Date: Jan. 4, 2011

(87) PCT Pub. No.: WO2009/155887
PCT Pub. Date: Dec. 30, 2009

(65) Prior Publication Data
US 2011/0207805 A1      Aug. 25, 2011

(30) Foreign Application Priority Data
Jun. 26, 2008 (CZ) ................. PV 2008-407

(51) Int. Cl.
*A61K 31/335* (2006.01)
*A61K 31/35* (2006.01)

(52) U.S. Cl.
USPC .......................................... 514/452; 514/456

(58) Field of Classification Search ............... 514/452, 514/456
See application file for complete search history.

(56) References Cited

U.S. PATENT DOCUMENTS

| | | | |
|---|---|---|---|
| 3,994,925 A | 11/1976 | Madaus et al. | |
| 4,081,529 A | 3/1978 | Crippa | |
| 4,764,508 A | 8/1988 | Gabetta et al. | |
| 4,886,791 A * | 12/1989 | Giorgi et al. | 514/100 |
| 4,895,839 A | 1/1990 | Bombardelli | |
| 5,196,448 A | 3/1993 | Ely | |
| 5,198,430 A | 3/1993 | Valcavi et al. | |
| 5,714,473 A | 2/1998 | Lentzen et al. | |
| 5,906,991 A | 5/1999 | Wachter et al. | |
| 5,912,265 A | 6/1999 | Bombardelli et al. | |
| 6,913,769 B2 | 7/2005 | Oslick et al. | |
| 6,967,031 B1 | 11/2005 | Oslick et al. | |

FOREIGN PATENT DOCUMENTS

| | | |
|---|---|---|
| CZ | 287657 | 12/1997 |
| CZ | 292832 | 4/2003 |

OTHER PUBLICATIONS

Arak Petrochemical Company, 2012.*
Bharate SS, Bharate SB, Bajaj AN. Interactions and incompatibilities of pharmaceutical excipients with active pharmaceutical ingredients: a comprehensive review. Journal of Excipients and Food Chemistry. 2010. 1(3), 3-26.*
Peters HJW. Lactose for Direct Compression. Chemsitry Weekly. Dec. 2009. 197-198.*

* cited by examiner

*Primary Examiner* — Paul Zarek
(74) *Attorney, Agent, or Firm* — Notaro, Michalos & Zaccaria P.C.

(57) ABSTRACT

The invention relates to a composition containing flavanolignans, e.g., isolated from *Silybum marianum*, and basic amino acids and, optionally, other auxiliary substances, in the form of mixture, and to the method of preparation of these compositions by mixing the components and their homogenization. The invention is applicable particularly in the pharmaceutical industry, cosmetics, food industry, breweries, distilleries, and in the industry of beverage production.

20 Claims, 1 Drawing Sheet

1 - silybin A, 2 - silybin B, 3 - isosilybin A, 4 - isosilybin B, 5 – silychristin, 6 – isosilychristin, 7 – silydianin, 8 - taxifolin

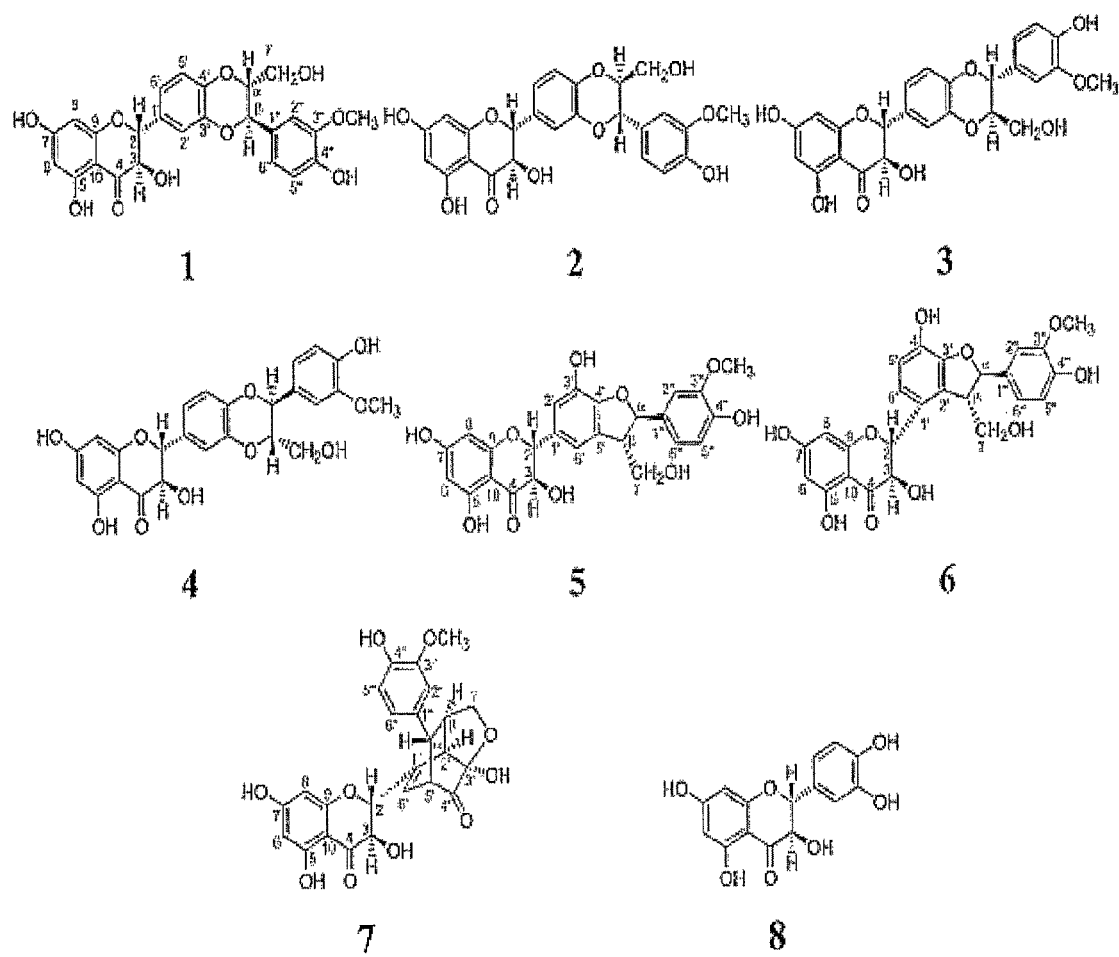
1 - silybin A, 2 - silybin B, 3 - isosilybin A, 4 - isosilybin B, 5 – silychristin, 6 – isosilychristin, 7 – silydianin, 8 - taxifolin

COMPOSITION OF FLAVANOLIGNAN AND AMINO ACID WITH IMPROVED WATER SOLUBILITY

TECHNICAL FIELD

The invention relates to compositions on the basis of flavanolignans and method of preparation thereof.

BACKGROUND ART

Extracts from the fruits of milk thistle (*Silybum marianum* (L.) Gaertn.) are known by their contents of the flavanolignan-type substances having polyhydroxyphenyl chromanone skeleton (G. Hahn et al., Arzneimittel—Forschung Drug Res. 18, 698-704, (1968)). These polyhydroxyphenyl chromanones comprise silybin and its enantiomers (silybin A, silybin B, isosilybin A, isosilybin B), silydianin, and silychristin that are altogether referred to as a powder extract of *Silybum marianum* or also as silymarin. The extract of *Silybum marianum*, CAS No: [84604-20-6] is almost insoluble in water, it is soluble in acetone, ethyl acetate, methanol, and ethanol. Qualitative requirements for the extract are defined, e.g., by the pharmacopoeia standards USP/NF or Ph Eur.

In practice also silybin, CAS No. [22888-70-6], chemical name 3,5,7-trihydroxy-2-[3-(4'-hydroxy-3'-methoxyphenyl)-2-hydroxymethyl)-1,4-benzodioxan-6-yl]-4-chromanone, of the molecular formula of $C_{25}H_{22}O_{10}$ and molecular weight 482.443, is used. The melting point of commercially available silybin is about 158° C. for anhydrous substance and about 167° C. for monohydrate.

However, all the herein above mentioned substances are very little soluble in aqueous media.

The solubility of silybin at 25° C. (mg/ml) in solvents miscible with water is as follows:

| | |
|---|---|
| Ethoxy diglycol | 350.1 ± 10.4 |
| Polyethylene glycol 200 | 345.9 ± 9.5 |
| Polyethylene glycol 400/ethanol (1:1) | 342.1 ± 7.1 |
| Ethanol | 225.2 ± 5.2 |
| Propylene glycol | 162.4 ± 3.6 |
| Water | 0.4 ± 0.1 |

The solubility of silybin at 25° C. (mg/ml) in solvents not fully miscible with water is as follows:

| | |
|---|---|
| Glyceryl monooleate | 33.2 ± 2.8 |
| Tocopherol | 20.0 ± 1.9 |
| Castor oil | 7.1 ± 1.2 |
| Ethyl linoleate | 2.1 ± 0.8 |
| Capryl-caprine triglyceride | 0.8 ± 0.5 |
| Fish oil | 0.5 ± 0.2 |

The silybin solubilities are given according to: Jong Soo Woo, Tae-Seo Kim, Jae-Hyun Park, and Sang-Cheol Chi: Formulation and Biopharmaceutical Evaluation of Silymarin Using SMEDDS. *Arch Pharm Res* Vol. 30, No 1, 82-89, 2007.

The phenolic nature of flavanolignans is given by the substitution by two hydroxyl groups in positions 5 and 7 on the 4-chromanone skeleton and by one hydroxyl group in position 4' on the side hydroxyl-methoxyphenyl group. Their dissociation constant pK values are as follows:

| | |
|---|---|
| silybin | $pKa.1_{[25°\,C.]} = 7.00$; $pKa.1_{[37°\,C.]} = 6.86$ |
| | $pKa.2_{[25°\,C.]} = 8.77$; $pKa.2_{[37°\,C.]} = 8.77$ |
| | $pKa.3_{[25°\,C.]} = 9.57$; $pKa.3_{[37°\,C.]} = 9.62$ |
| silychristin | $pKa.1_{[25°\,C.]} = 6.52$; $pKa.1_{[37°\,C.]} = 6.62$ |
| | $pKa.2_{[25°\,C.]} = 7.22$; $pKa.2_{[37°\,C.]} = 7.41$ |
| | $pKa.3_{[25°\,C.]} = 8.96$; $pKa.3_{[37°\,C.]} = 8.94$ |
| silydianin | $pKa.1_{[25°\,C.]} = 6.64$; $pKa.1_{[37°\,C.]} = 7.10$ |
| | $pKa.2_{[25°\,C.]} = 7.78$; $pKa.2_{[37°\,C.]} = 8.93$ |
| | $pKa.3_{[25°\,C.]} = 9.66$; $pKa.3_{[37°\,C.]} = 10.06$ |

The pK value data are quoted according to: Meloun, Milan; Syrový, Tomáš; Bordovská, Sylva; Vrána, Aleš: Reliability and uncertainty in the estimation of $pK_a$ by least squares nonlinear regression analysis of multiwavelength spectrophotometric pH titration data. *Analytical and Bioanalytical Chemistry*, 2007, 387 (3), 941-955.

All substances mentioned above exhibit a broad spectrum of pharmacologic activities: antioxidant properties, stabilization of cell membranes, stimulation of protein biosyntheses. These effects constitute the basis for utilization of silymarin and its components, particularly silybin (a mixture of silybins A and B and even isosilybins A and B) as a hepatoprotective agent. Silymarin acts against both acute and chronic liver intoxication by many toxins, demonstrably by carbon tetrachloride, galactose amine, paracetamol, ethanol, phalloidin, and α-amanitin. Silymarin is thus an active component of many preparations used for the therapy and prevention of liver diseases (LEGALON®, FLAVOBION®, etc.). More information on recent research on silybin and silymarin and their use can be found in survey paper by Křen V., Walterová D.: Silybin and silymarin—new effects on applications. *Biomed. Papers* 149 (1), 29-41, 2005.

The powder extract of *Silybum marianum* used for the preparation of hepatoprotective pharmaceutical preparations or food additives is a refined extract with the standardized content of flavanolignans. According to USP/NF it should contain 40-80% of flavanolignans sum, evaluated by liquid chromatography to silybin standard. According to the recent studies, the therapeutic potential of the *Silybum marianum* substances can be used, along to the traditional hepatoprotective effects, particularly for prophylactic enhancement of the health condition of people endangered by diabetes and colon cancer.

Experimental studies on hypoglemic effects of *Silybum marianum* (Males R. J., Farnsworth N. R.: Antidiabetic plants and their active constituents. *Phytomedicine* 2 (2), 137-189, 1995) and on positive effects of flavanolignanes on diabetes (Soto C. P. et al.: C. *Pharmacology, Toxicology & Endocrinology*, 119 (2), 125-129, 1998) have been published.

Use of flavanolignans from *Silybum marianum* as adjuvants in the chemotherapy of tumours (U.S. Pat. No. 5,714,473) and as antiproliferative medicaments (U.S. Pat. No. 5,912,265) has been recently protected by patents.

Silymarin in the form of silymarin methylglucamine is also proposed as a component of preparations against the effects of alcohol (U.S. Pat. Nos. 6,913,769 a 6,967,031).

Use of the flavanolignans of *Silybum marianum* in medicaments as well as in other applications in which they affect particularly the sensoric properties of products such as their taste and colour is limited by their low solubility in both hydrophilic and lipophilic solvents.

A number of approaches have been proposed for overcoming this insufficient solubility such as, e.g., by the preparation of silymarin component salts with N-methylglucamine (U.S. Pat. No. 3,994,925). These salts with monoamino polyhydroxyalkyl alcohols hydrolyze easily, thus they require stabilization with a substantial amount of polyvinyl pyrrolidone or albumin. Similarly, a procedure comprising preparing the solution of silymarin flavanolignans in polyvinyl pyrrolidone and lyophilising this solution has also been proposed (U.S. Pat. No. 4,081,529).

Esters of silybin with dicarboxylic acids, e.g., with disodium salt of bis-hemisuccinate of silybin according to U.S. Pat. No. 5,196,448, are destined for dermatologic and cosmetic applications in topic application forms.

The preparation of silybin glycosides that are more soluble in water than silybin and exhibit similar effects as silymarin is protected by the CZ Patent 287 657. However, the industrial production of glycosides is technologically demanding and costly.

Complex compounds of silymarin or silybin with phospholipids, described in U.S. Pat. Nos. 4,764,508 and 4,895,839, are prepared by dissolving the components (1 mol of silymarin or silybin and 0.3 to 2.0 mol of phosphatidyl choline, phosphatidyl serine, or phosphatidyl ethanol amine) in an aprotic solvent (dioxane or acetone) and by precipitating the complex by adding an aliphatic hydrocarbon or by lyophilisation or spray drying. In addition to the ecologically undesirable utilization of organic solvents, the resulting complex compounds form disperse systems in contact with water. This feature orientates the application of these complex compounds more to the topic preparations.

Inclusion complexes of silybin with cyclodextrins are described in U.S. Pat. No. 5,198,430. Complexes of silybin with α-, β- and γ-cyclodextrin and their derivatives in molar ratio 1 mol of silybin to 1 to 4 mol of the respective cyclodextrin have been described. The complexes are prepared by dissolving the two components in aqueous ammonia and by removal of ammonia either by evaporation or neutralization by hydrochloric acid and by subsequent drying or lyophilisation. For the preparation of these inclusion complexes physiologically unsuitable ketonic solvents such as acetone, cyclohexanone, methylisobutyl ketone, and diethyl ketone are used, the residual amounts of which in the complexes must be monitored and removed. The thus prepared complexes exhibit a better biological availability than the flavanolignans themselves, however, their solubility in water is enhanced but very little so that anion-active tensides should be used in drug forms.

A procedure based on dissolving the flavanolignanes of *Silybum marianum* in an alkanolic or ketonic solvent and mixing this solution with an auxiliary substance from the group of tetritols, pentitols, hexitols, or vinylpyrrolidonic or ethylene oxide homopolymers and the subsequent removal of the solvents (CZ Patent 292 832) prevents the formation of crystalline forms causing the low solubility. The solid drug forms prepared from the thus obtained substances exhibit better dissolution parameters, but they are not water soluble in the exact meaning of the word.

Processes for enhancing the bioavailability of silymarin based on the preparation of co-precipitates of flavanolignans with carriers and detergents are covered by a patent (U.S. Pat. No. 5,906,991). Water-soluble saccharides, derivatives of cellulose, and polyvinylpyrrolidon are described as suitable carriers, polysorbates of fat acids are used as detergents. In the dissolution test these co-precipitates exhibit a higher solubility than the non-modified silymarin so that their higher bioavailibility can be expected.

The so far known water-soluble forms of the *Silybum marianum* extract are not fully suitable for application in food industry, e.g., for use in beverages like beer, beverages on the basis of beer, and soft drinks, as some of their components are not approved for use in food industry.

DISCLOSURE OF THE INVENTION

The object of the invention is a flavanolignan-based composition containing a) flavanolignans of the general formula I

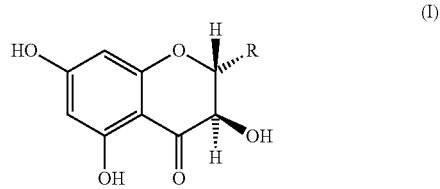

wherein
R is

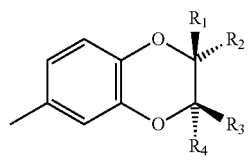

wherein $R_1$ is H, $R_2$ is $CH_2OH$, $R_3$ is 4-hydroxy-3-methoxyphenyl, $R_4$ is H, or $R_1$ is $CH_2OH$, $R_2$ is H, $R_3$ is H, $R_4$ is 4-hydroxy-3-methoxyphenyl, or $R_1$ is H, $R_2$ is 4-hydroxy-3-methoxyphenyl, $R_3$ is $CH_2OH$, $R_4$ is H, or $R_1$ is 4-hydroxy-3-methoxyphenyl, $R_2$ is H, $R_3$ is OH, $R_4$ is H, or R is

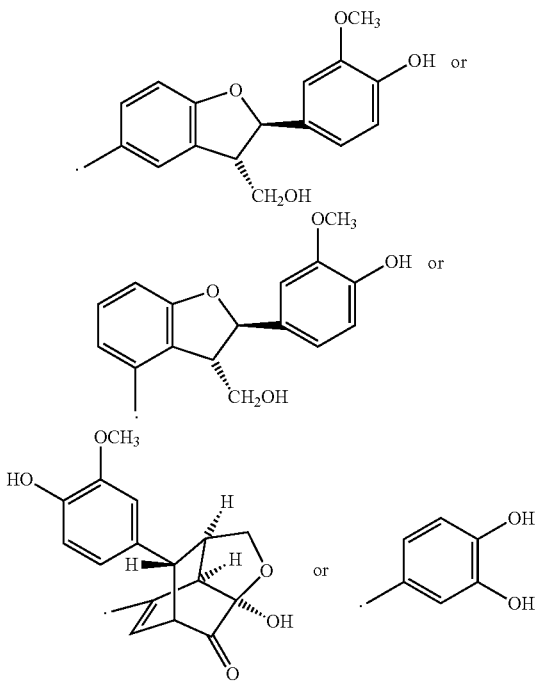

or their mixtures
and b) at least one substance selected from the group comprising basic amino acids or their mixtures in the molar ratio a:b=1:1 to 1:2.

In a preferred embodiment of the invention the flavanolignans of the general formula I are selected from the group comprising isomers of silybin, silydianin and silychristin, or their mixture consisting of 20 to 45 wt. % of silydianin and silychristin sum, 40 to 65 wt. % of silybin A and silybin B sum, 10 to 20 wt. % of isosilybin A and isosilybin B sum.

Preferably, the basic amino acid is selected from the group comprising L-lysine, racemic lysine, L-arginine, racemic arginine, L-ornithine, and racemic ornithine. L-histidine or racemic histidine are particularly advantageous for the alkalinity adjustment of the final mixture of flavanolignans with basic amino acids. L-histidine (CAS No. 71-00-1) and L-lysine (CAS No. 39665-12-8) are essential amino acids for humans.

For instance, mixtures of silybin with selected basic amino acids according to this invention in the molar ratios 1:2 to 1:1 in the final mixture without any auxiliary substances represent concentrations within the limits (silybin concentrations are given in wt. %):

Silybin/L-lysine 59.50 to 74.61%; Silybin/L-arginine 58.07 to 73.47%

Silybin/L-ornithine 64.62 to 80.59%; Silybin/L-histidine 60.86 to 75.66%.

When dissolving the mixtures according to the invention in water it is necessary to take into consideration the different solubilities of the basic amino acids themselves. At room temperature the following solutions of the amino acids in water can be easily prepared: 1.0 M solution of L-lysine (14.62 vol. %), 0.5 M solution of L-arginine (8.71 vol. %), or 0.25 M solution of L-histidine (3.88 vol. %).

L-arginine (CAS No. 74-79-3) is essential only for children having a deficiency in one of the urea cycle enzymes but generally it is not considered an essential amino acid though it is nutritionally valuable for the organism. Also L-ornithine (CAS No. 60259-81-6) is not generally considered essential for human beings but in the organism it can substitute arginine. These amino acids are commercially available in the form of free bases, they are well soluble in water and they have a relatively favourable sweet taste.

The values of dissociation constants pK and pI of the basic amino acids according to the invention in aqueous solutions at 25° C.:

| Amino acid | $pK_1$ | $pK_2$ | $pK_3$ | pI |
|---|---|---|---|---|
| L-arginine | 2.01 | 9.04 | 12.48 | 10.76 |
| L-histidine | 1.77 | 6.10 | 9.18 | 7.64 |
| L-lysine | 2.18 | 8.95 | 10.53 | 9.47 |
| L-ornithine | 1.71 | 8.69 | 10.76 | 9.73 | pI = ½ ($pK_i$ + $pK_{i+1}$), i = 2 for all amino acids mentioned above.

The pK and pI values are quoted according to: CRC Handbook of Chemistry and Physics, 66th ed., CRC Press, Boca Raton, Fla. 1985; R. M. C. Dawson, D. C. Elliott, W. H. Elliott, K. M. Jones, Data for Biochemical Research 3rd ed., Clarendon Press Oxford 1986.

The mixtures of flavanolignans with basic amino acids according to the invention are by an order of magnitude more soluble in water than the individual flavanolignans. The fact that for their use they need not be declared as new chemical entities is another advantage of the mixtures according to the invention. The dry extract of *Silybum marianum* denoted as Silymarin contains certain amounts of oligomers of its components that do not react easily with the basic amino acids so that they can cause opalescence or even a moderate turbidity of the solution.

It is well known that under the action of strong bases such as NaOH or KOH the gamma-pyrone ring opens and derivatives of hydroxyl carboxylic acids are formed (Wawzonek S./Heterocyclic Compounds, Vol. 2, page 383-385, Ed. R. Elderfield, J. Wiley, New York 1951). The amino acids in the mixture according to this invention act on the flavanolignans more gently than the inorganic bases and they are very stable in a solid physical mixture.

In another aspect of the invention, the composition according to this invention can contain one or more auxiliary substances. The water-soluble substances not exhibiting hygroscopicity, destined for use in compositions that are applied in liquid form, can be used as such auxiliary substances. Preferably, the so-called alcoholic sugars—tetritols, pentitols, or hexitols, namely treitol, erythritol, arabinitol, xylitol, talitol, or mannitol, can be used. Furthermore, also polyethylene glycols 4000 to 20 000, preferably polyethylene glycol 6000 dried by spraying, can be used for this purpose. Moreover, the substances affecting the physical properties of the mixture as, e.g., the electrostatic charge, flowability, or volume weight, can be used as auxiliary substances. These auxiliary substances are useful particularly for the solid drug forms. E.g., the amorphous silicon dioxide or amorphous magnesium aluminometasilicate $Al_2O_3$—$MgO.-1.7SiO_2$-$xH_2O$ can be such auxiliary substances.

The mixtures of flavanolignans with basic amino acids can be used for the preparation of solid application forms of flavanolignans such as, e.g., capsules or tablets with an enhanced biological accessibility, from which the addition compositions according to the invention are formed under physiologic conditions in the digestive system. Preferably, such solid application forms of flavanolignans are prepared in the acid-resistant form, by coating the tablets or capsules with a layer resistant to the effects of gastric juice for the prescribed period of time.

Another aspect of the invention is a method of preparation of a mixture for flavanolignan-based compositions, wherein the flavanolignan of the general formula I and a substance selected from the group comprising basic amino acids and their mixtures are mixed in the molar ratio of from 1:1 to 1:2. The homogenous mixtures are preferably prepared in the presence of at least one auxiliary substance.

FIGURES

FIG. 1 represents the structures of silymarin components: 1-silybin A, 2-silybin B, 3-isosilybin A, 4-isosilybin B, 5-silychristin, 6-isosilychristin, 7-silydianin, 8-taxifolin.

EXAMPLES OF CARRYING OUT THE INVENTION

In the following the invention is illustrated by way of examples that, however, do not limit its scope in any way.

Example 1

Water-Soluble 48% Extract of *Silybum Marianum*

Charge Composition:

| | |
|---|---|
| Silymarin 80% | 1200.00 g |
| L-arginin 98% | 711.03 g |
| Polyethylene glycol 6000 | 88.97 g |

A weighted amount of the commercially available silymarin is mixed with anhydrous L-arginin and made up to 2000 g by spray-dried polyethylene glycol 6000 and then sieved through a sieve of the mesh of 0.25 mm. After homogenization on a laboratory mixer ERWEKA, the homogeneous product is filled into packing protecting against light and air humidity.

Solubility of individual components of flavanolignans in the mixture according to Example 1

| Solvent | Silychristin | Silydianin | Silybin A | Silybin B | Isosylibin | Σ mg/L |
|---|---|---|---|---|---|---|
| Purified water | 258.24 | 214.66 | 178.41 | 289.05 | 112.90 | 1053.25 |
| Buffer solution pH 4.5 * | 241.57 | 189.31 | 127.95 | 209.62 | 78.63 | 847.08 |

\* Buffer solution according to Bates with sodium acetate and hydrochloric acid of the ionic strength of 0.05 adjusted by potassium chloride.

Example 2

Water-Soluble Mixture of 40% Sylibin with L-Lysine 490.00 g of 98% silybin of the grain size less then 100 μm is mixed with 370.00 g of finely ground erythritol and then 340.00 g of finely ground 97% L-lysine monohydrate and sieved through a sieve of the mesh of 0.25 mm. After homogenization on a laboratory mixer ERWEKA the homogeneous product of the weight of 1200 g is filled into packing protecting against light and air humidity.

Example 3

Silymarin 110 Mg Capsules

Charge Composition

| | |
|---|---|
| Silymarin 80% | 16.075 kg |
| L-histidine | 10.345 kg |
| Aerosil 200 VV | 0.580 kg |

A mixture of silymarin and Aerosil, sieved through a sieve of the mesh of 0.25 mm on a sieve Frewitt SGV, is transferred into the Turbulla T 50A homogenizer of the working vessel volume of 55 litres and L-histidine is added. The charge is mixed for 14 minutes at 15 rpm.

The homogeneous mixture is filled into gelatine size No 1 capsules in the amount of 225 mg per capsule. The content of silymarin in the capsule, expressed as silybin, amounts to minimum 110 mg.

Example 4

Coated Silybin Capsules

Composition of One Capsule:

| | |
|---|---|
| Silybin 98% | 120.611 mg |
| L-arginine | 87.101 mg |
| Polyethylene glycol 6000 | 41.288 mg |
| Aerosil 200 VV | 1.000 mg |

A mixture of silybin and Aerosil, sieved through a sieve of the mesh of 0.25 mm on a sieve Frewitt SGV, is transferred into the Turbulla T 50A homogenizer of the working vessel volume of 55 liters and L-arginine and powdered polyethylene glycol 6000 are added. The charge is mixed for 14 minutes at 15 rpm.

The homogeneous mixture is tableted on a rotational tablet machine FETTE P 1200; the weight of the tablet core is 250 mg.

Outward form: Circular yellow pills of the diameter of 9 mm, concave, the upper die with a dividing groove. The tablets are coated with an acid-resistant coating in a drum Glatt GMPC II. The coating amounts to 4% of the tablet core weight. The weight of the coated tablet is 260 mg.

| Coating parameters | Core heating | Coating | Drying | Cooling |
|---|---|---|---|---|
| Inlet air temperature [° C.] | 80 | 65 | 50 | 25 |
| Outlet air temperature [° C.] | 65 | 50 | 40 | 25 |
| Drum speed [rpm] | 3 | 12 | 4 | 2 |
| Air volume [m³/h] | 750 | 1000 | 1000 | 750 |
| Pressure at the jet [bar] | 0 | 2 | 0 | 0 |

INDUSTRIAL APPLICABILITY

The invention relates to composition and methods of preparation of solid mixtures containing flavanolignans isolated from *Silybum marianum* and basic amino acids that exhibit a substantially better solubility in water in comparison with pure flavanolignans. Due to their physiologically favorable activity such mixtures can be used for the preparation of medicaments with better biological accessibility and for food supplements, or for the standardization or fortification of the polyphenolic compound contents or contents of essential amino acids that are natural components of beers and other beverages on the basis of beer. By their agreeable bitter taste and intensely yellow color these addition compounds are also useable as tonic substances and natural dyestuffs for non-alcoholic as well as alcoholic beverages.

The invention is generally applicable particularly in pharmaceutical industry, cosmetics, food industry, breweries, distilleries, and in the industry of beverage preparation.

The invention claimed is:

1. Flavanolignan-based composition, characterized in that it contains:

a) flavanolignans of the general formula I

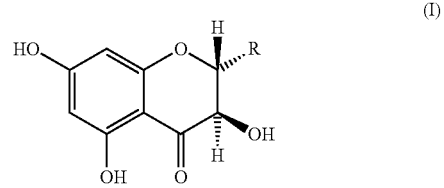

wherein
R is

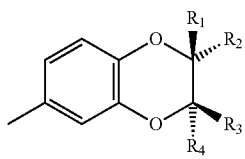

wherein $R_1$ is H, $R_2$ is $CH_2OH$, $R_3$ is 4-hydroxy-3-methoxyphenyl, $R_4$ is H, or $R_1$ is $CH_2OH$, $R_2$ is H, $R_3$ is H, $R_4$ is 4-hydroxy-3-methoxyphenyl, or $R_1$ is H, $R_2$ is 4-hydroxy-3-methoxyphenyl, $R_3$ is $CH_2OH$, $R_4$ is H, or $R_1$ is 4-hydroxy-3-methoxyphenyl, $R_2$ is H, $R_3$ is OH, $R_4$ is H, or R is

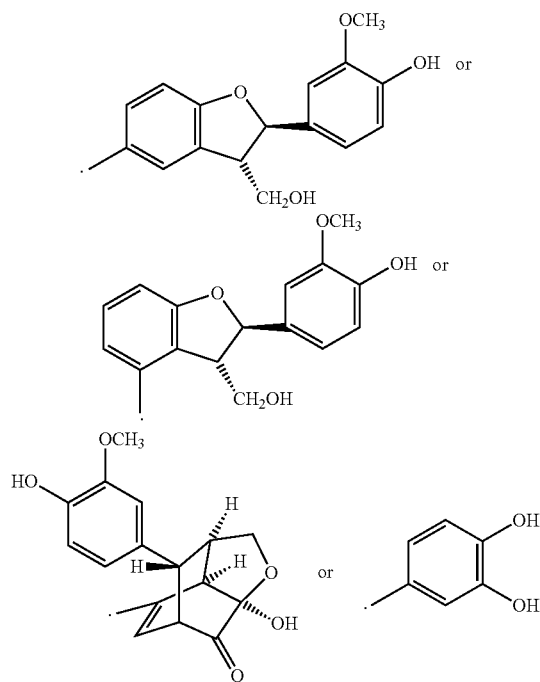

or their mixtures
and
  b) at least one substance selected from the group comprising basic amino acids and their mixtures in molar ratio a:b=1:1 to 1:2.

2. The composition according to claim 1, characterized in that the flavanolignans of the general formula I are selected from the group comprising silybin, silidianin, and silychristin, or their mixture consisting of 20 to 45 wt. % of silydianin and silychristin sum, 40 to 65 wt. % of silybin A and silybin B sum, and of 10 to 20 wt. % of isosilybin A and isosilybin B sum.

3. The composition according to claim 1, characterized in that the basic acid is selected from the group comprising L-histidine, racemic histidine, L-lysine, racemic lysine, L-arginine, racemic arginine, L-ornithine and racemic ornithine.

4. The composition according to claim 1, characterized in that it further contains one or more auxiliary substances.

5. The composition according to claim 4, characterized in that the auxiliary substance is a water-soluble auxiliary substance not exhibiting hygroscopicity.

6. The composition according to claim 4, characterized in that the auxiliary substance is a substance affecting the physical properties of the mixture.

7. Method of preparation of the composition according to claim 1, characterized in that flavanolignan of the general formula I and a substance selected from the group comprising basic amino acids and their mixtures are mixed in molar ratio 1:1 to 1:2 and the resulting mixture is homogenized.

8. The method according to claim 7, characterized in that the mixture is prepared in the presence of at least one auxiliary substance.

9. The composition according to claim 4, characterized in that the auxiliary substance is a water-soluble auxiliary substance not exhibiting hygroscopicity comprising alcoholic sugars.

10. The composition according to claim 4, characterized in that the auxiliary substance comprises polyethylene glycols 4 000 to 20 000.

11. The composition according to claim 4, characterized in that the auxiliary substance is selected from the group comprising amorphous silicon dioxide and amorphous magnesium aluminometasilicate $Al_2O_3$—$MgO.1.7SiO_2$-$xH_2O$.

12. Flavanolignan-based physical mixture, characterized in that it contains:
  a) flavanolignans of the general formula I

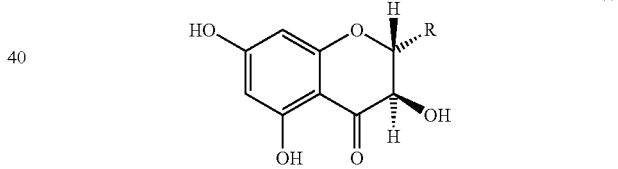

(I)

wherein
R is

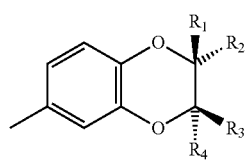

wherein $R_1$ is H, $R_2$ is $CH_2OH$, $R_3$ is 4-hydroxy-3-methoxyphenyl, $R_4$ is H, or $R_1$ is $CH_2OH$, $R_2$ is H, $R_3$ is H, $R_4$ is 4-hydroxy-3-methoxyphenyl, or $R_1$ is H, $R_2$ is 4-hydroxy-3-methoxyphenyl, $R_3$ is $CH_2OH$, $R_4$ is H, or $R_1$ is 4-hydroxy-3-methoxyphenyl, $R_2$ is H, $R_3$ is OH, $R_4$ is H, or R is

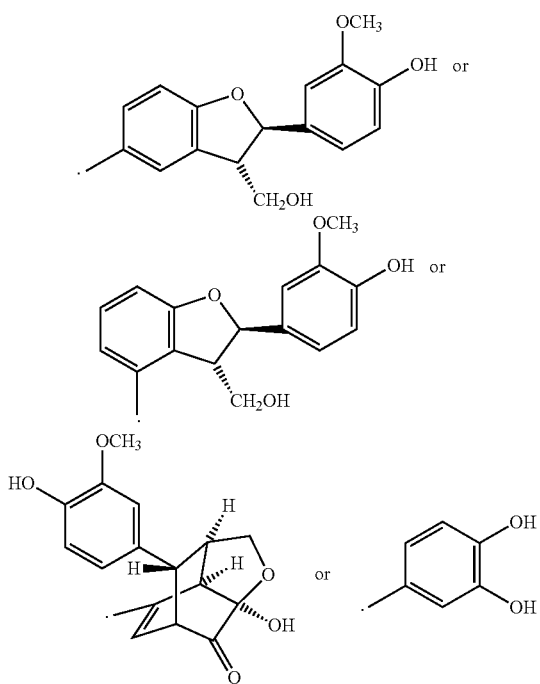

or their mixtures
and b) at least one substance selected from the group comprising basic amino acids and their mixtures in molar ratio a:b=1:1 to 1:2;

wherein the flavanolignan and the substance selected from the group comprising basic amino acids and their mixtures are physically intermixed, and substantially do not form salts.

13. The physical mixture to claim 12, characterized in that the flavanolignans of the general formula I are selected from the group comprising silybin, silidianin, and silychristin, or their mixture consisting of 20 to 45 wt. % of silydianin and silychristin sum, 40 to 65 wt. % of silybin A and silybin B sum, and of 10 to 20 wt. % of isosilybin A and isosilybin B sum.

14. The physical mixture to claim 12, characterized in that the basic acid is selected from the group comprising L-histidine, racemic histidine, L-lysine, racemic lysine, L-arginine, racemic arginine, L-ornithine and racemic ornithine.

15. The physical mixture according to claim 12, characterized in that it further contains one or more auxiliary substances.

16. The physical mixture according to claim 15, characterized in that the auxiliary substance is a water-soluble auxiliary substance not exhibiting hygroscopicity.

17. The physical mixture according to claim 15, characterized in that the auxiliary substance is a substance affecting the physical properties of the mixture.

18. The physical mixture according to claim 15, characterized in that the auxiliary substance is a water-soluble auxiliary substance not exhibiting hygroscopicity comprising alcoholic sugars.

19. The physical mixture according to claim 15, characterized in that the auxiliary substance comprises polyethylene glycols 4 000 to 20 000.

20. The physical mixture according to claim 15, characterized in that the auxiliary substance is selected from the group comprising amorphous silicon dioxide and amorphous magnesium aluminometasilicate $Al_2O_3$—$MgO.1.7SiO_2$-$xH_2O$.

* * * * *